(12) United States Patent
Gerzenshtein et al.

(10) Patent No.: US 12,734,015 B2
(45) Date of Patent: Sep. 15, 2026

(54) MEDICAL IMAGING DEVICE ATTACHMENT APPARATUS FOR A CANNULA

(71) Applicant: GMD Medical Development and Engineering, LLC, Lakeland, FL (US)

(72) Inventors: Jacob Gerzenshtein, Lakeland, FL (US); John Mallas, Laotto, IN (US); Jeremy DeWitt, Lakeland, FL (US)

(73) Assignee: GMD Medical Development and Engineering, LLC, Lakeland, FL (US)

(*) Notice: Subject to any disclaimer, the term of this patent is extended or adjusted under 35 U.S.C. 154(b) by 511 days.

(21) Appl. No.: 18/321,959

(22) Filed: May 23, 2023

(65) Prior Publication Data

US 2024/0390107 A1 Nov. 28, 2024

(51) Int. Cl.

*A61B 90/57* (2016.01)
*A61B 17/34* (2006.01)
*A61B 90/00* (2016.01)

(52) U.S. Cl.

CPC .......... *A61B 90/57* (2016.02); *A61B 17/3421* (2013.01); *A61B 90/361* (2016.02)

(58) Field of Classification Search

CPC ... A61B 90/57; A61B 17/3421; A61B 90/361; A61B 8/46; A61B 8/4405

See application file for complete search history.

(56) References Cited

U.S. PATENT DOCUMENTS

| | | | | |
|---|---|---|---|---|
| 5,623,931 | A * | 4/1997 | Wung | A61B 17/3403 600/461 |
| 11,490,925 | B1 * | 11/2022 | Alsufyani | A61B 8/4444 |
| 2013/0072816 | A1 * | 3/2013 | Girgenti | A61B 10/0275 600/567 |
| 2015/0320298 | A1 * | 11/2015 | Missov | A61B 90/50 248/51 |
| 2019/0059940 | A1 * | 2/2019 | Cohen | A61B 17/3423 |
| 2025/0176994 | A1 * | 6/2025 | Zine | A61B 8/4218 |

* cited by examiner

*Primary Examiner* — Matthew Kremer
*Assistant Examiner* — Aaron Merriam
(74) *Attorney, Agent, or Firm* — Lewellyn Law, PLLC; Stephen Lewellyn

(57) ABSTRACT

An apparatus for attaching a medical imaging device to a cannula for conjoined movement with the cannula to allow simultaneous manipulation of the imaging device and the cannula with one hand during an image-guided medical procedure. The image-guided medical procedure may be a liposuction procedure. The apparatus may have a cannula handle assembly, a rigid extension arm, and a probe holder assembly. The handle assembly is configured to removably receive and hold a cannula and the probe holder assembly is configured to removably receive and hold an imaging probe. The extension arm is connected at one end to the handle assembly and at its other end to the probe holder assembly to position an imaging probe with its imaging end approximate to and facing the cannula tip so that the cannula tip can be imaged by the probe during a procedure.

17 Claims, 10 Drawing Sheets

MEDICAL IMAGING DEVICE ATTACHMENT APPARATUS FOR A CANNULA

TECHNICAL FIELD

The present disclosure relates generally to medical imaging devices and cannulas and, more particularly, to an apparatus for attaching a medical imaging device probe to a cannula for image-guided medical procedures using the cannula.

BACKGROUND

A liposuction cannula, also known as a liposuction wand, is a surgical instrument used in liposuction procedures to remove excess fat from the body. It is a long, thin, and hollow tube made of stainless steel or plastic, with a small opening at the end. The wand is attached to a suction machine that creates a vacuum, which allows the surgeon to remove fat cells from specific areas of the body, such as the abdomen, thighs, hips, arms, and neck. During the procedure, the surgeon makes small incisions in the skin and inserts the cannula through these incisions, guiding it to the targeted fat cells.

The harvested fat can be reintroduced into the body for various purposes such as grafting to add volume. However, blindly reintroducing the fat places the patient at risk of violating the fascia covering the underlying muscle. The underlying muscle contains large vessels, and penetrating the muscle puts the patient at risk for injection of fat into vessels. This may result in fatality because of a fat embolus/emboli.

To mitigate these risks, ultrasound guidance is utilized to ensure that the operator stays in the correct layer and avoids penetration of the fascia/muscle, thereby avoiding complications. Utilizing ultrasound imaging technology during liposuction procedures provides the surgeon with real-time visualization of the targeted area, enabling them to make more precise incisions and reduce the risk of injury to surrounding tissues.

Image-guided liposuction, which incorporates ultrasound guidance, is a minimally invasive surgical procedure that uses medical imaging technologies such as ultrasound to guide the liposuction process. The surgeon uses imaging technology to visualize the fat deposit and surrounding tissues, allowing for precise and controlled removal of fat by the cannula. This technique can be particularly useful in treating areas where there is deep fat, or in areas with fibrous tissues or scar tissue, which can make traditional liposuction more challenging. Image-guided liposuction also reduces the risk of damage to surrounding tissues, as the surgeon can see exactly where the cannula is placed.

Therefore, there is a need for a system to attach an ultrasound imaging probe to a liposuction cannula for image-guided liposuction that allows a surgeon to manipulate the cannula and imaging probe simultaneously with one hand, while also ensuring safe and precise reintroduction of fat for grafting purposes.

SUMMARY

The present disclosure provides an apparatus for attaching an imaging device to a cannula for conjoined movement with the cannula for image-guided medical procedures. In aspects, the apparatus is particularly useful in image-guided liposuction procedures.

In an embodiment, a medical imaging probe attachment apparatus has a cannula handle assembly, a rigid extension arm, and a probe holder assembly. The cannula handle assembly has a cannula clamp that is configured to removably attach a cannula to the cannula handle assembly for conjoined movement with the cannula handle assembly and with the cannula extending in a cannula direction outwardly from the cannula handle assembly along a cannula axis. The rigid extension arm has opposite first and second ends and a length extending therebetween. The rigid extension arm is attached at its first end to the cannula handle assembly for conjoined movement with the cannula handle assembly and with the rigid extension arm extending outwardly from the cannula handle assembly in the cannula direction and at a spaced lateral distance from and parallel to the cannula axis. The probe holder assembly has a probe attachment that is configured to removably attach an imaging probe to the probe holder assembly with an imaging end of the imaging probe being located approximate to and facing in a direction toward a distal end of the cannula when the cannula is attached to the cannula handle assembly.

In embodiments, the probe holder assembly may have an attachment fixture and a probe attachment subassembly. The attachment fixture is attached to the second end of the rigid extension arm for conjoined movement with the cannula handle assembly. The probe attachment subassembly is attached to the attachment fixture, and the probe attachment subassembly has the probe attachment. The probe attachment subassembly may slidingly connected to the attachment fixture to allow selective positioning of the probe attachment subassembly relative to the attachment fixture.

In embodiments, the probe attachment subassembly may have a float member and a guide member. The float member may have the probe attachment. The float member may be operatively connected to the guide member such that the float member is capable of constrained up and down movement along a direction toward and away from the cannula axis. The float member may be spring biased in a direction toward the cannula axis.

In embodiments, the rigid extension arm may be adjustably connected at its first end to the cannula handle assembly to selectively the length of the extension arm extending from the cannula handle assembly. The first end of the rigid extension arm may be slidingly disposed in a bore formed in the cannula handle assembly and an extension arm clamp may be provided to clamp the first end selected in position in the bore.

Numerous additional objects, features, and advantages of the present invention will be readily apparent to those of ordinary skill in the art upon a reading of the following detailed description of presently preferred, but nonetheless illustrative, embodiments of the present invention when taken in conjunction with the accompanying drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods, and systems for carrying out the several purposes of the present invention. It is important, therefore, that the claims be regarded as including such equivalent constructions insofar as they do not depart from the spirit and scope of the present invention.

For a better understanding of the invention, its operating advantages, and the specific objects attained by its uses, reference should be had to the accompanying drawings and descriptive matter in which there are illustrated embodiments of the invention.

DETAILED DESCRIPTION

Figure 1:
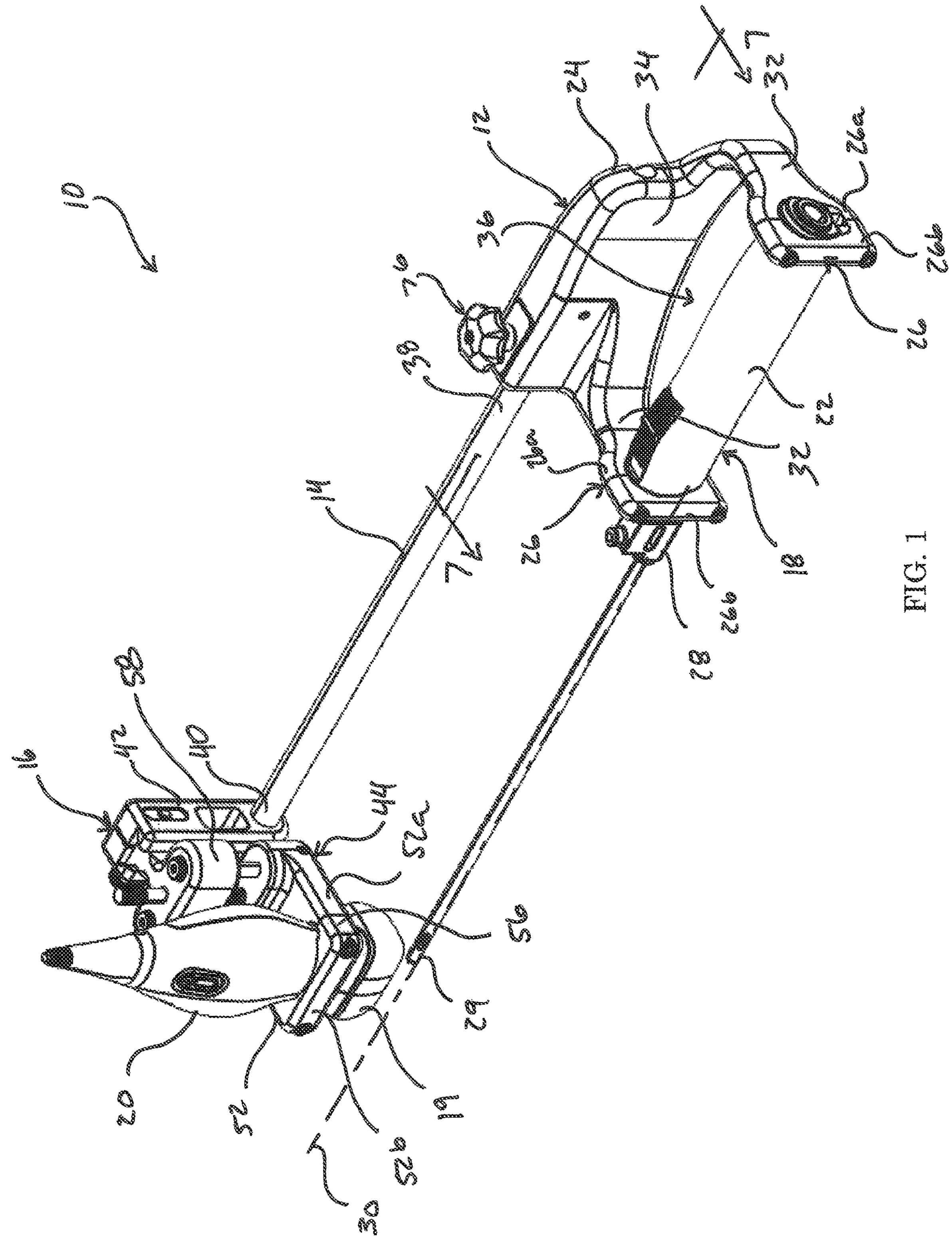
FIG. 1 is a perspective view of an apparatus for attaching an imaging device to a cannula according to an embodiment of the present disclosure, shown with the apparatus attaching an imaging device to a cannula.
Figure 2:
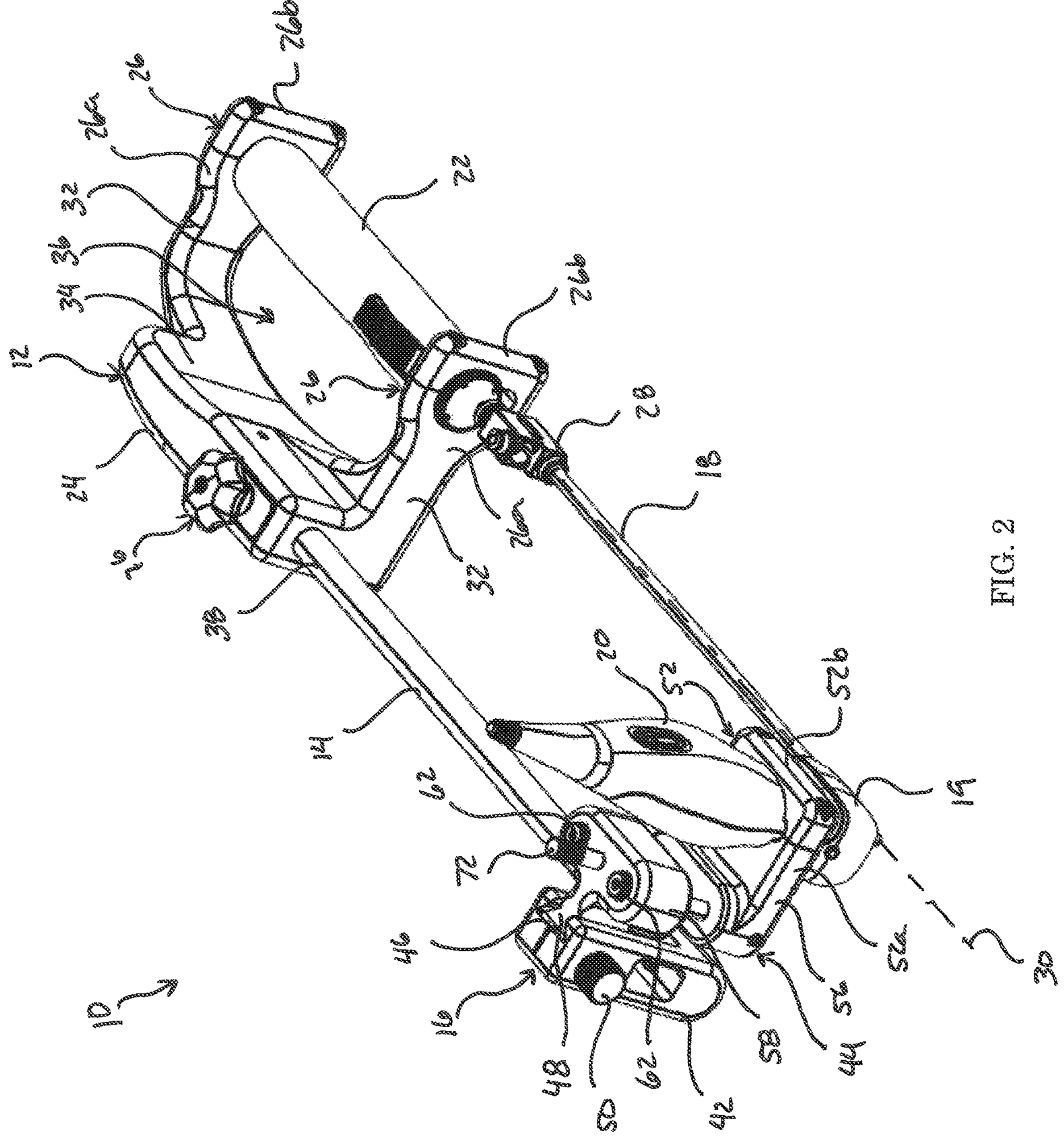
FIG. 2 is a second perspective view of the apparatus.
Figure 3:
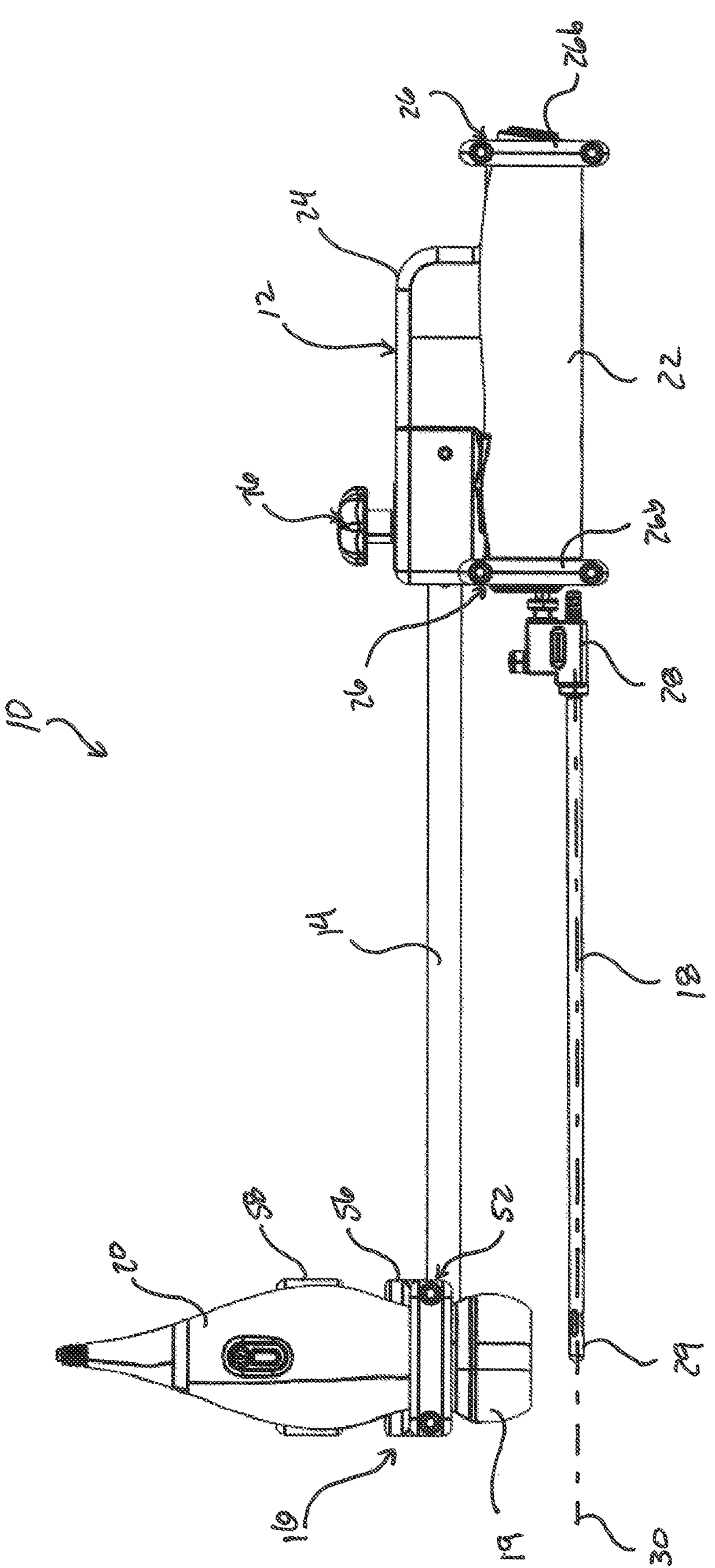
FIG. 3 is a front view of the apparatus.
Figure 4:
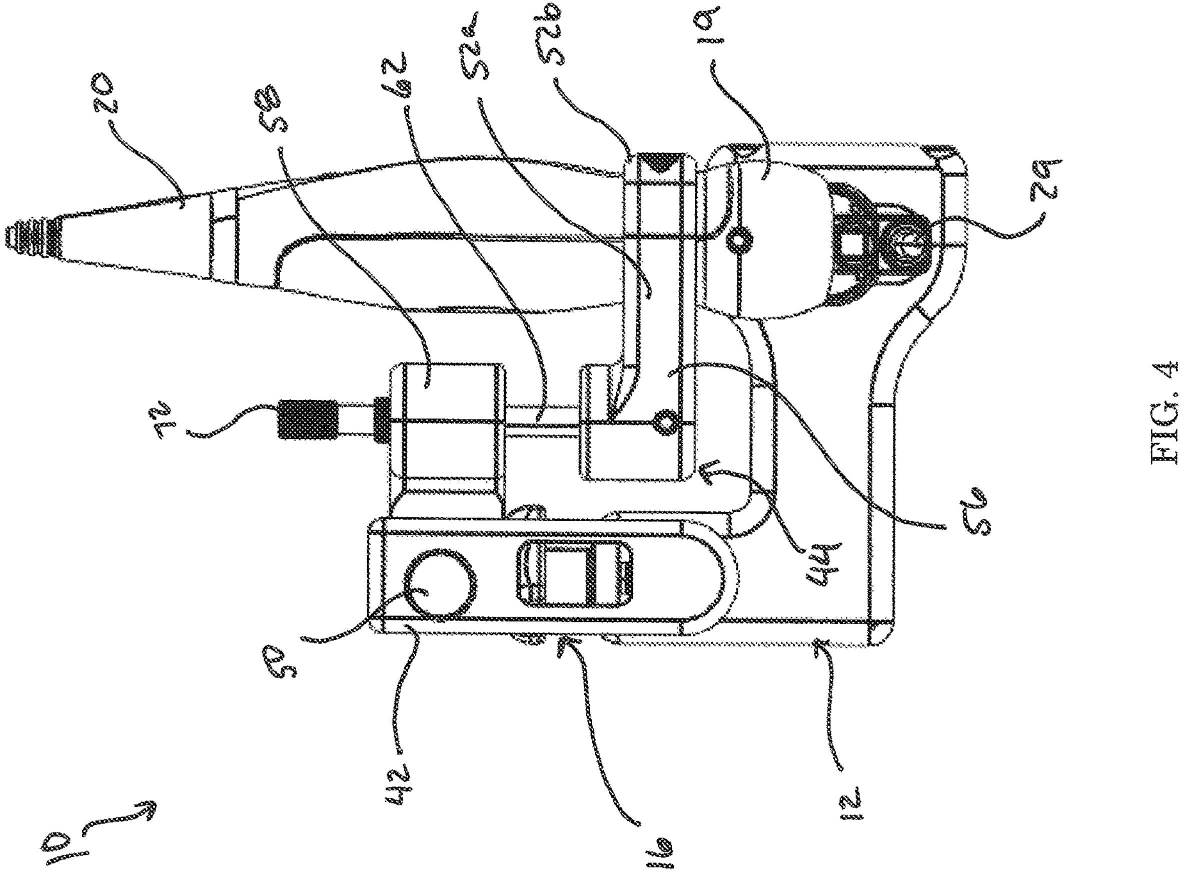
FIG. 4 is an end view of the apparatus.
Figure 5:
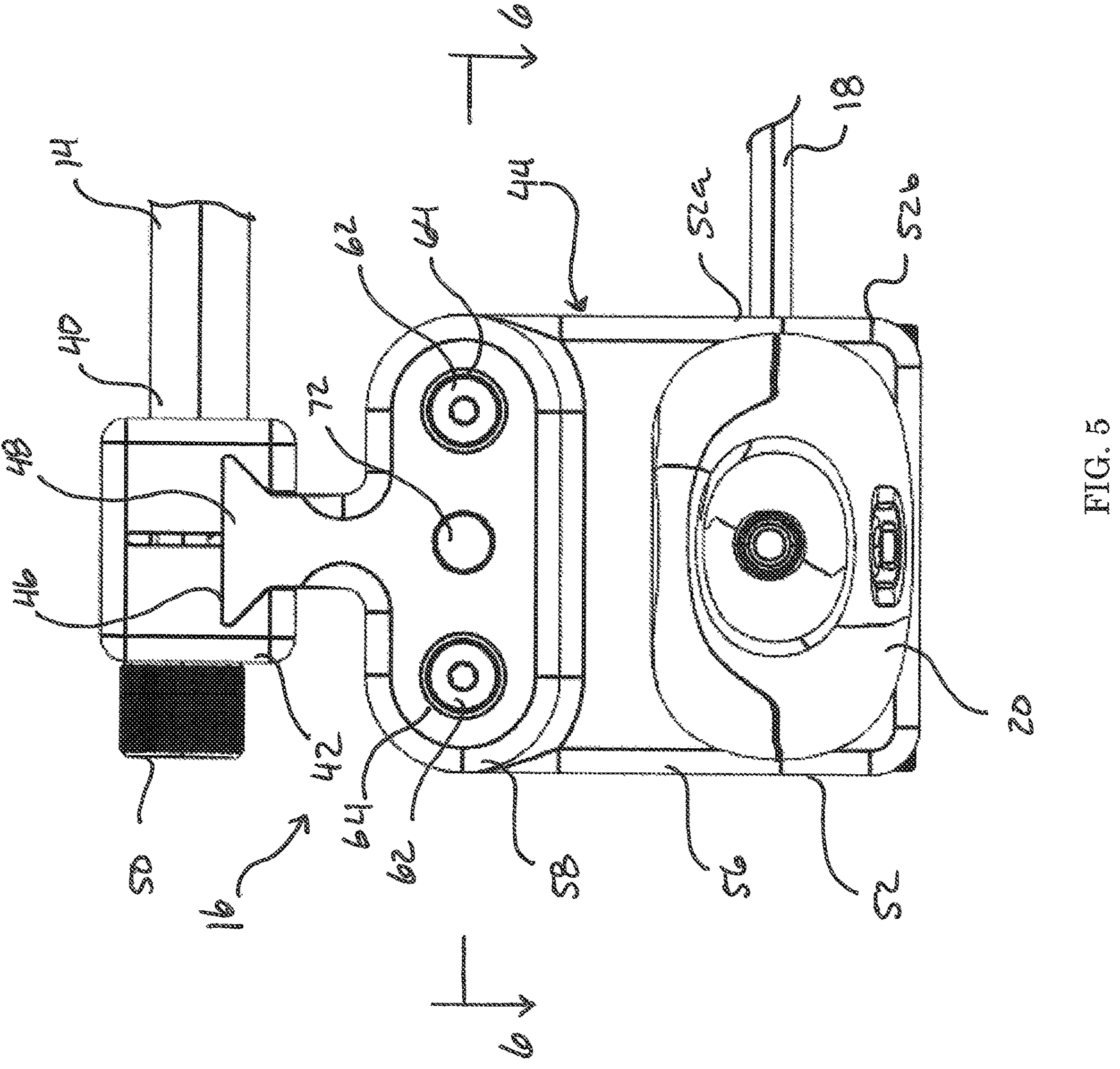
FIG. 5 is an enlarged top view of the apparatus, showing details of a probe holder assembly attached to an end of an extension arm and holding a probe of an imaging device.

This description and the accompanying drawings that illustrate inventive aspects, embodiments, implementations, or applications should not be taken as limiting—the claims define the protected invention. Various mechanical, structural, and operational changes may be made without departing from the spirit and scope of this description and the claims. In some instances, well-known devices, structures, or techniques have not been shown or described in detail in order not to obscure the invention. Like reference numbers in two or more figures represent the same or similar elements.

It should be understood that although this description is made to be sufficiently clear, concise, and exact, scrupulous and exhaustive linguistic precision is not always possible or desirable, since the description should be kept to a reasonable length and skilled readers will understand background and associated technology.

In addition, the singular forms "a", "an", and "the" are intended to include the plural forms as well, unless the context indicates otherwise. And, the terms "comprises", "includes", "has", and the like specify the presence of stated features, steps, operations, elements, and/or components but do not preclude the presence or addition of one or more other features, steps, operations, elements, components, and/or groups.

Further, specific words chosen to describe one or more embodiments and optional elements or features are not intended to limit the invention. For example, spatially relative terms-such as "beneath", "below", "lower", "above", "upper", "proximal", "distal", and the like—may be used to describe one element's or feature's relationship to another element or feature as illustrated in the figures. These spatially relative terms are intended to encompass different locations (i.e., translational placements) and orientations (i.e., rotational placements) of a device in use or operation in addition to the location and orientation shown in the figures.

For example, if a device in the figures is turned over, elements described as "below" or "beneath" other elements or features would then be "above" or "over" the other elements or features. Thus, the exemplary term "below" can encompass both locations and orientations of above and below. A device may be otherwise oriented (e.g., rotated 90 degrees or at other orientations) and the spatially relative descriptors used herein interpreted accordingly. Likewise, descriptions of movement along (translation) and around (rotation) various axes include various special device locations and orientations. The combination of a body's location and orientation defines the body's pose.

Aspects of the present disclosure provide an apparatus for attaching a medical imaging device to a cannula for image-guided medical procedures that allow for manipulation of the cannula and the imaging probe simultaneously with one hand. The apparatus of the present disclosure is particularly useful for attaching an ultrasound probe to a liposuction cannula for image-guided liposuction that allows a surgeon to manipulate the cannula and imaging probe simultaneously with one hand.

Turning to FIGS. 1-8, an illustrative embodiment of the imaging device attachment apparatus 10 is shown. The apparatus 10 has a cannula handle assembly 12, an extension arm 14, and an imaging device probe holder assembly 16. The apparatus 10 is representatively shown in use in connection with a power-assisted liposuction cannula 18 secured by the cannula handle assembly 12, and an ultrasound imaging probe 20 secured by the imaging device probe holder assembly 16.

Apparatus 10 is configured to position probe 20 in a location approximate to the working end or distal end of the cannula so that the probe can image the distal end to guide the position of the distal end during a medical procedure. Importantly, apparatus 10 is further configured to fixedly hold the probe 20 and the cannula 18 for conjoined movement such that a user can grasp the cannula handle 22 and manipulate the cannula and imaging probe simultaneously with one hand.

Figure 8:
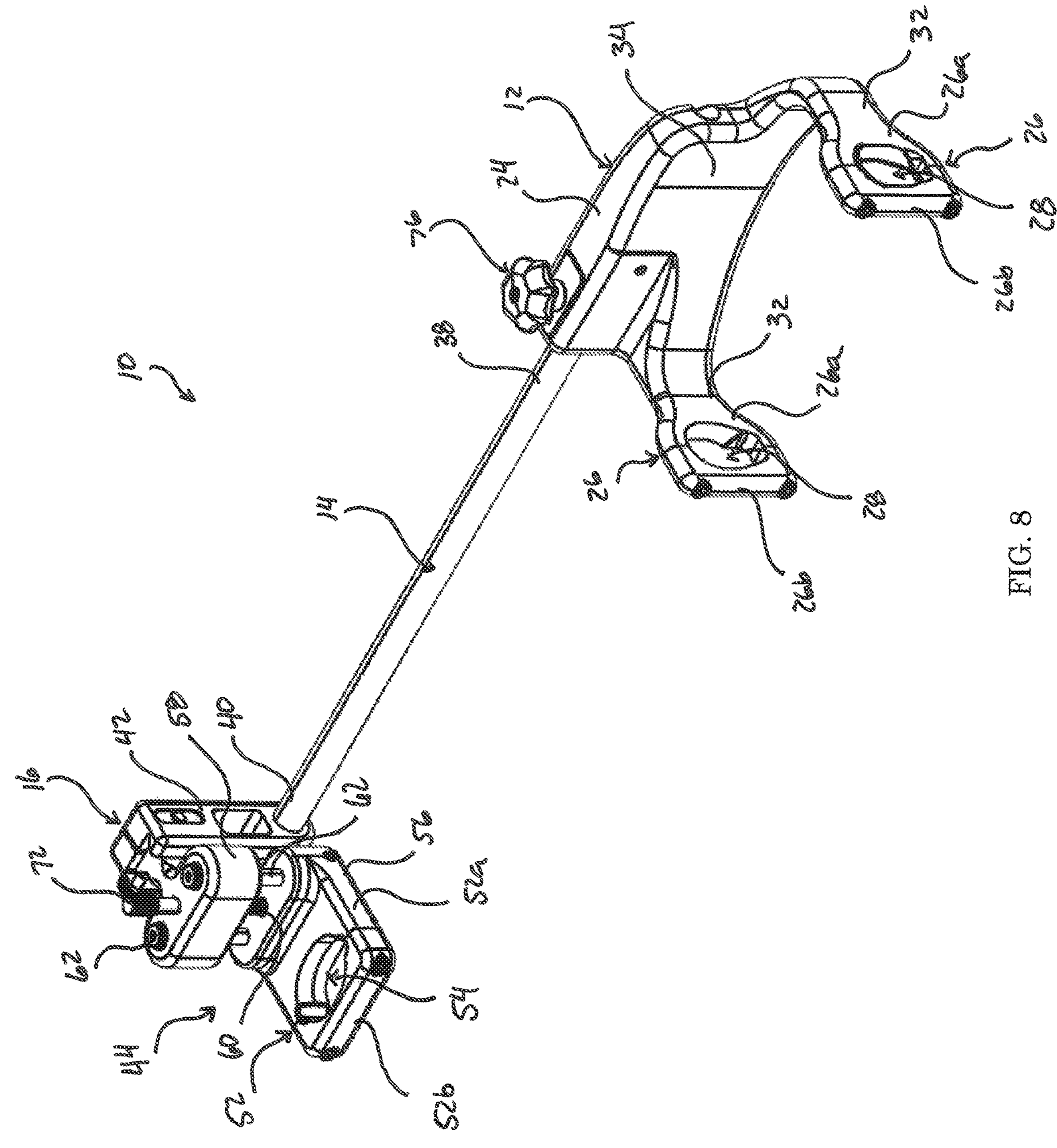
FIG. 8 is a perspective view of an apparatus for attaching an imaging device to a cannula according to an embodiment of the present disclosure, shown not attaching an imaging device to a cannula.

The cannular handle assembly 12 has a housing or body 24 that is configured to receive and retain the cannula in a fixed relation with the body for conjoined movement with the body. In the representatively shown embodiment, body 24 has a pair of spaced clamps 26 that are configured to receive and secure the cannula handle 22 at respective forward and reward positions along the cannula handle. Clamps 26 may be split-type clamps that have two cooperatively parts 26*a* and 26*b* that are joinable by threaded fasteners for example, and when joined define an aperture 28 in which the cannula handle 22 is received and retained, as best seen in FIG. 8. The aperture 28 can be provided with a desired profile that can conform to the profile of the cannula handle 22 at the location where the handle is to be secured by the clamp. In the representatively illustrated embodiment, clamp part 26*a* can be formed integral with the body 24 and part 26*b* can be secured to clamp part 26*a* by a pair of threaded fasteners.

When the cannula 18 is securely attached to the handle assembly 14 at the proximal end 28 thereof via the cannula handle 22, the cannula extends in a direction outwardly from the handle assembly along a cannula axis 30. For the purpose herein, cannula axis is fixed in space in relation to the handle assembly 14 and the cannula generally extends along the cannula axis 30. During use, depending on the material of the cannula 18, the cannula may deflect in space away from the cannula axis 30, but the cannula axis remains fixed relative to the handle assembly 14.

As further shown, clamps 26 are disposed at the ends of spaced leg members 32 of the body 24 which are joined at the opposite ends by a center portion 34. The center portion 34 is spaced from the clamps 26 such that when the cannula 18 is secured to the handle assembly 14 a hand space 36 is provided between the cannular handle and the center portion to allow a user's hand to properly grasp the cannula handle without interference by the body 24.

Extension arm 14 is rigid and has opposite ends 38 and 40 and a length extending between the ends. The extension arm 14 is attached at end 38 to the handle assembly 12 for conjoined movement therewith and such that the extension arm extends outwardly from the handle assembly in the same direction as the cannula and with its length at a spaced lateral distance from and parallel to the cannula axis 30. In this manner, end 40 of the rigid extension arm 14 fixed at the spaced lateral distance from the cannula axis 30.

The probe holder assembly 16 is attached to end 40 of the extension arm 14 for conjoined movement with the handle assembly 12 via the extension arm. The probe holder assembly is configured to removably receive and retain an imaging probe, representatively the ultrasound probe 20 with its imaging end being 19 located an approximate spaced distance from and facing in a direction toward the distal end 29 of the cannula 18.

In the representatively illustrated embodiment, the probe holder assembly 16 may have an attachment fixture 42 and a probe clamp subassembly 44. The attachment fixture 42 is configured to fixedly attach to the end 40 of the extension arm 14. The subassembly 44 is configured to attach to the attachment fixture 42. The fixture 42 and the subassembly 44 may be configured to allow the subassembly to be adjustably fixed at selective positions to the fixture in a direction that is perpendicular to the cannula axis 30. Such adjustability may be desired to adjust distance between the imaging end 19 of the probe 20 and the distal end 29 of the cannula 18.

In the representatively illustrated embodiment, the attachment fixture 42 may have a dove-tail shaped slot 46 arranged with its length extending in a direction perpendicular to the cannula axis and the subassembly 44 may have a correspondingly dove-tail shaped projection 48 that is slidingly received in the slot for selectively positioning therealong. Slot 46 may be provided by partially separated body portions of the fixture that can be pulled together by a threaded fastener 50 to clamp the projection 48 at a fixed, selected position along the slot.

The probe holder assembly 16 has a probe clamp 52 that is configured to receive and secure the imaging probe 18 to the subassembly. In the representatively illustrated embodiment, probe clamp subassembly 44 may have the probe clamp 52. Clamp 52 may be a split-type clamp that has two cooperatively parts 52*a* and 52*b* that are joinable by threaded fasteners for example, and when joined define an aperture 54 in which the probe 20 is received and retained. Aperture 54 can be provided with a desired profile that can conform to the profile of the probe 20 at the location where the probe is to be secured by the clamp.

It is contemplated that multiple probe holder assemblies 16 and/or related subassemblies 44 could be provided, each with aperture 54 having a different profile to correspond to differently shaped imaging probes to allow a simple exchange between depending on the imaging probe being used.

Further, in the representatively illustrated embodiment, the probe clamp subassembly 44 may have float member 56 and a guide member 58. The float member 56 has the probe clamp 52 to receive and secure the imaging probe 20 to the float member. The float member 56 is operatively connected to the guide member 58 such that the float member is capable of constrained up and down movement along a direction toward and away from the guide member or toward and away from the cannula axis 30. The float member 56 may be spring biased in a direction away from the guide member by a spring element, such as spring 60, which biases the float member in a direction toward the cannula axis 30.

The advantage of this arrangement is it allows the probe 20 to float up and down as the probe is moved along the surface of the patient to automatically adjust the distance between the imaging head of the probe and the distal end 29 of the cannula to correspond to the relative depth of the cannula in the patient. While apparatus 10 can be provided without such an arrangement, the arrangement is desired to allow a greater freedom of movement of the cannula during the medical procedure.

Figure 6:
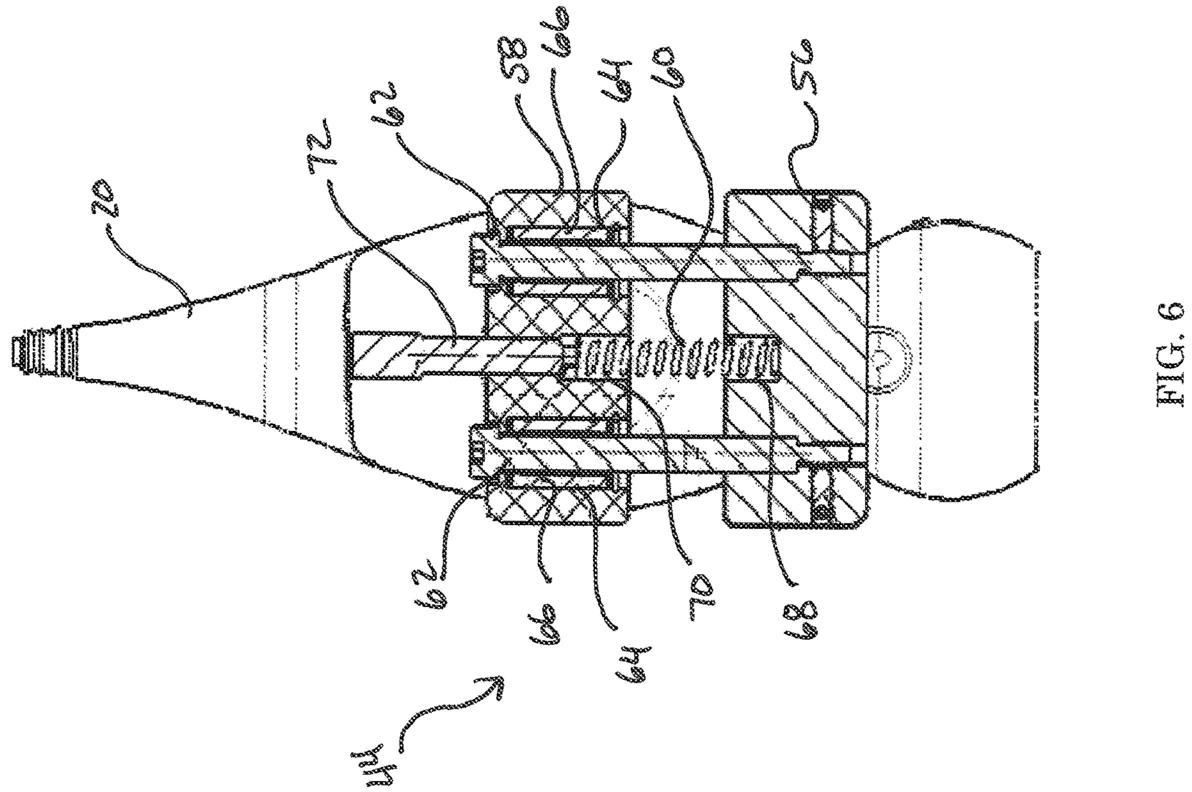
FIG. 6 is a cross-sectional view through a probe holder assembly taken along line 6-6 in FIG. 5.

As best seen in FIG. 6, in the representatively illustrated embodiment, a pair of spaced guide pins 62 slidingly connect the float member 56 and the guide member 58. In an aspect, one end of each guide pin 62 may be fixedly attached to the float member and each pin may slidingly extend through a corresponding bore 64 through the guide member 58. Each bore 64 may be sleeved with a linear bearing 66. Each guide pin 62 may be a shoulder bolt that is passed through the bore 64 and then threadedly attached to the float member. The head of the shoulder bolt constrains removal of the pin from the bore, which otherwise would result in a decoupling between the float member and the guide member.

Further compression spring 60 may extend between the float member 56 and the guide member 58 with an end of the spring received in a blind bore 68 formed in the float member and the opposite end of the spring received in bore 70 in the guide member. The spring 60 may be held in bore 70 by a tensioner 72 that is threadedly received by the bore. Tensioner 72 abuts the end of the spring 60 in bore 70 and turning the tensioner in a first direction causes the spring to compress to increase spring tension and the resulting biasing force of the spring against the float member. The biasing force can be reduced by turning the tensioner 70 in the opposite direction. Increasing the biasing force, increases the pressure or force required on the imaging probe for it translate or move relative to the cannula distal end 29.

Figure 7:
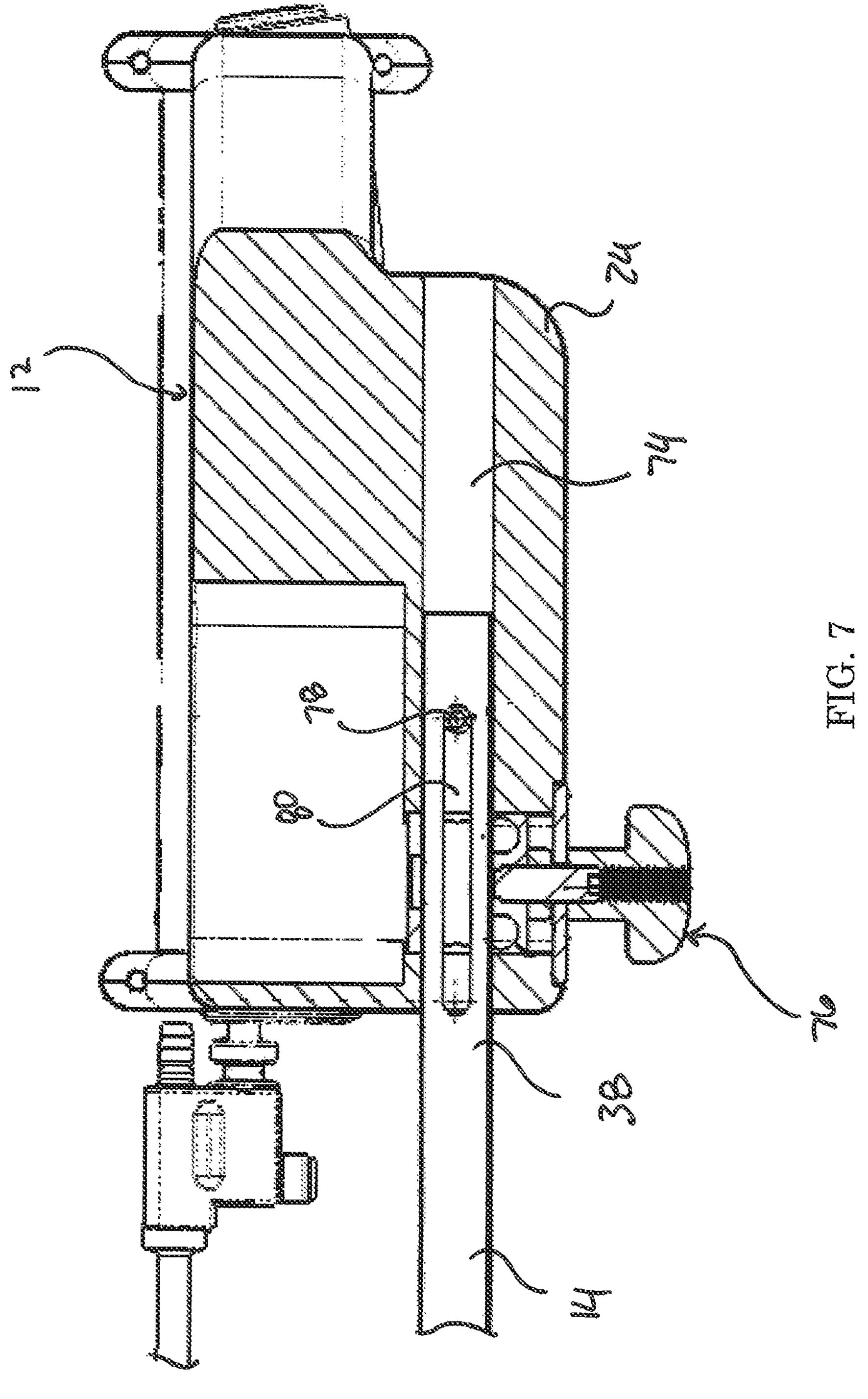
FIG. 7 is a cross-sectional view through a cannula handle assembly taken along line 7-7 in FIG. 1.

In an aspect, the extension arm 14 may be adjusted to selectively position the imaging probe 20 in a direction toward or away from the cannula handle assembly 12 to accommodate for various length cannulas. As best seen in FIG. 7, end 38 of the extension arm 14 may be slidingly disposed in bore 74 in the body 24 of the cannula handle assembly 12. Extension arm 14 may be pushed into bore 74 to shorten its length that extends from the cannula handle assembly and may be pulled from the bore to increase its length that extends from the handle assembly. A clamp element 76 can operatively engage the extension arm 14 to hold the extension arm in a desired telescopic position in bore 74. In an aspect, the distance the extension arm 14 can be telescoped in bore 74 can be restrained by a pin 78 being slidingly disposed in a slot 80 formed through the extension arm.

Figure 9:
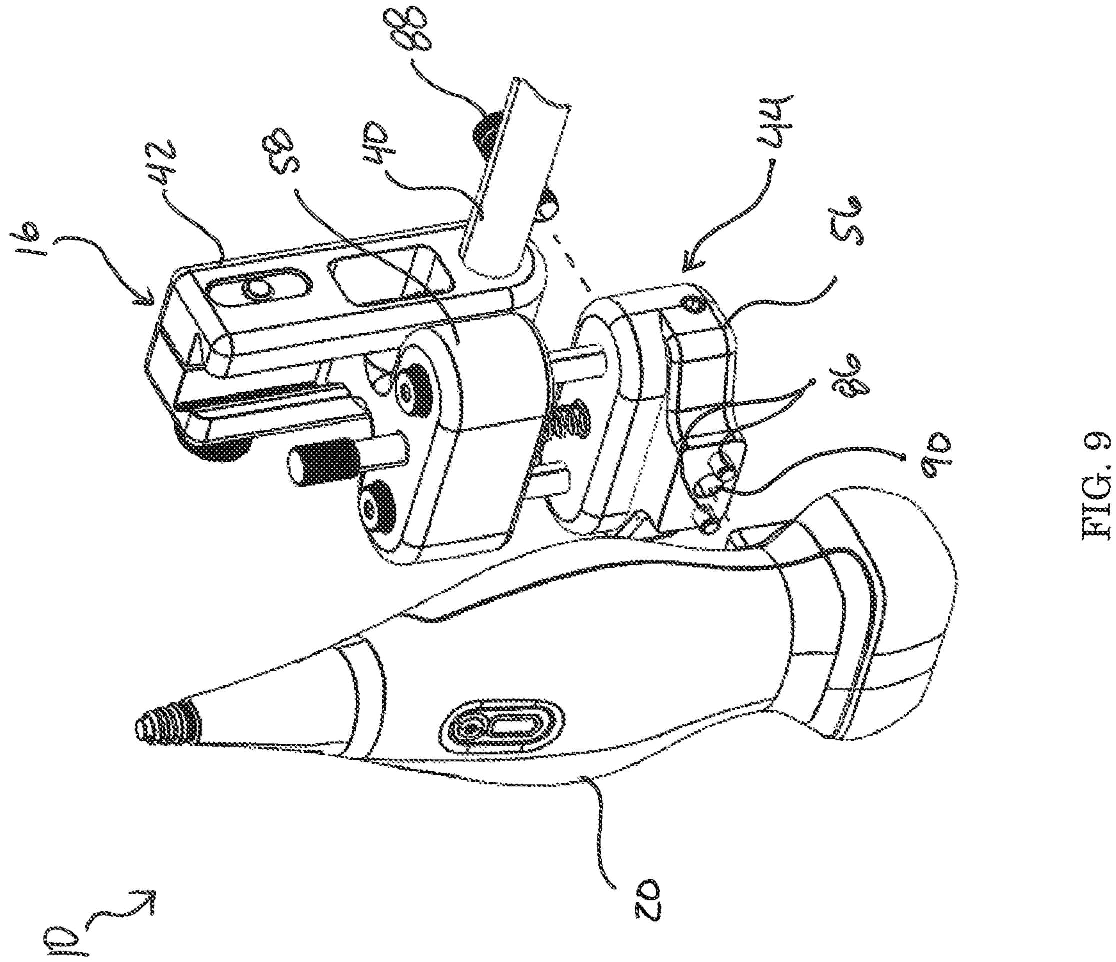
FIG. 9 is a first perspective view of an embodiment of the present disclosure, showing an alternative attachment for attaching an imaging probe to the apparatus.
Figure 10:
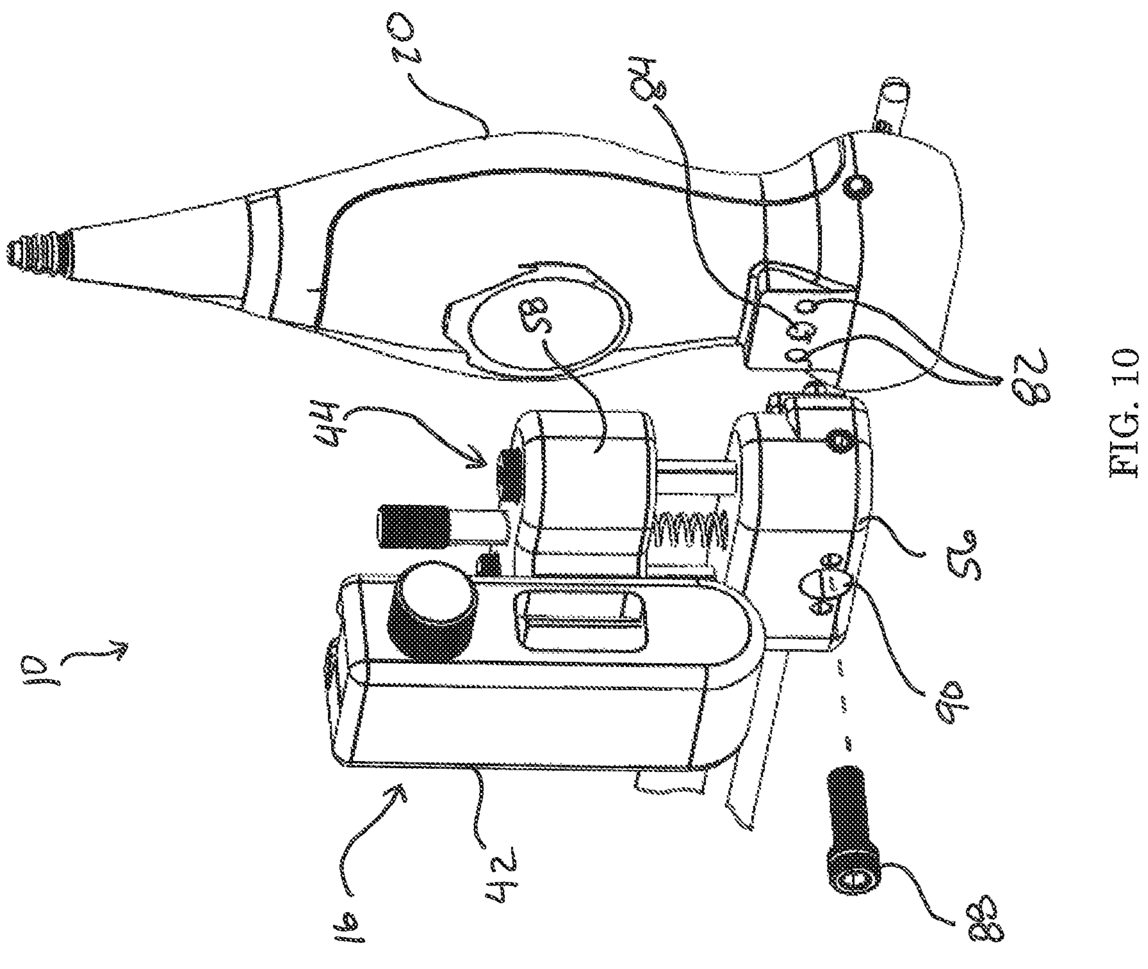
FIG. 10 is a second perspective view of an embodiment of the present disclosure, showing an alternative attachment for attaching an imaging probe to the apparatus.

FIGS. 9 and 10 illustrate apparatus 10 having an alternative arrangement for attaching the imaging probe 20. Here the probe clamp 52 is replaced by an alternative configuration for attaching the imaging probe 20 to the probe holder assembly 16. As representatively shown, the imaging probe 20 may be provided with one or more boss receiving apertures 82 and a threaded bore 84. The probe holder assembly 16 may be provided with one or more bosses 86 that are positioned to be received by a corresponding aperture 82 on the imaging probe to connect the imaging probe to assembly 16. A threaded fastener 88 is inserted through bore 90 and threaded into bore 84 to removably secure or attach the imaging probe to probe assembly 16 for conjoined movement therewith.

In the representatively illustrated embodiment, the one or more bosses 86 may be provided on the float member 56 and the bore 90 formed through the float member. To this end, the imaging probe 20 may be attached to the float member 56 for conjoined movement therewith.

The use of apparatus 10 may include adjustably positioning the imaging probe 20 relative to the cannula tip or distal end 29, inserting the cannula into a patient, such as to perform a liposuction procedure, contacting the patient's skin with the imaging probe while viewing the placement of the cannula tip in real time inside the patient on a monitor. Manipulating the imaging probe and the cannula is performed conjointly and simultaneously by a surgeon using one hand during the procedure.

While the disclosure has been illustrated and described in detail in the drawings and foregoing description, such illustration and description are to be considered exemplary and not restrictive in character, it being understood that illustrative embodiments have been shown and described and that all changes and modifications that come within the spirit of the disclosure are desired to be protected. It will be noted that alternative embodiments of the present disclosure may not include all the features described yet still benefit from at least some of the advantages of such features. Those of ordinary skill in the art may readily devise their own implementations that incorporate one or more of the features of the present disclosure and fall within the spirit and scope of the present invention as defined by the appended claims.

What is claimed is:

1. A medical imaging probe attachment apparatus, comprising:

a cannula handle assembly, the cannula handle assembly including a pair of spaced cannula clamps configured to receive and secure a cannula handle at spaced locations along the cannula handle for conjoined movement with the cannula handle assembly and with a cannula attached to the cannula handle extending in a cannula direction outwardly from the cannula handle assembly along a cannula axis, the cannula handle assembly further including a central portion extending between the spaced cannula clamps and defining a hand space between the central portion and the cannula handle when secured by the cannula clamps to permit a user to grasp the cannula handle for manipulation of the medical imaging probe attachment apparatus;

a rigid extension arm having opposite first and second ends and a length extending therebetween, the rigid extension arm attached at its first end to the cannula handle assembly for conjoined movement with the cannula handle assembly, the rigid extension arm extending outwardly from the cannula handle assembly in the cannula direction and at a spaced lateral distance from and parallel to the cannula axis; and a probe holder assembly, the probe holder assembly attached to the second end of the rigid extension arm for conjoined movement with the cannula handle assembly, the probe holder assembly having a probe attachment that is configured to removably attach an imaging probe to the probe holder assembly with an imaging end of the imaging probe being located approximate to and facing in a direction toward a distal end of the cannula when the cannula is attached to the cannula handle assembly.

2. The medical imaging probe attachment apparatus of claim 1, wherein the probe holder assembly has an attachment fixture and a probe attachment subassembly, the attachment fixture being attached to the second end of the rigid extension arm for conjoined movement with the cannula handle assembly, the probe attachment subassembly being attached to the attachment fixture, and the probe attachment subassembly having the probe attachment.

3. The medical imaging probe attachment apparatus of claim 2, wherein the probe attachment subassembly is slidingly connected to the attachment fixture to allow selective positioning of the probe attachment subassembly relative to the attachment fixture.

4. The medical imaging probe attachment apparatus of claim 2, wherein the probe attachment subassembly has a float member and a guide member, the float member has the probe attachment, the float member is operatively connected to the guide member such that the float member is capable of constrained up and down movement along a direction toward and away from the cannula axis.

5. The medical imaging probe attachment apparatus of claim 4, wherein the float member is spring biased in a direction toward the cannula axis.

6. The medical imaging probe attachment apparatus of claim 1, wherein the rigid extension arm is adjustably connected at its first end to the cannula handle assembly to selectively adjust the length of the extension arm extending from the cannula handle assembly.

7. The medical imaging probe attachment apparatus of claim 6, wherein the first end of the rigid extension arm is slidingly disposed in a bore formed in the cannula handle assembly, and further comprising an extension arm clamp that operates to clamp the first end in position in the bore.

8. The medical imaging probe attachment apparatus of claim 1, wherein the pair of spaced cannula clamps are separate from one another, and each includes an aperture in which the cannula handle is removably receivable to attach the cannula handle to the cannula handle assembly for the conjoined movement with the cannula handle assembly.

9. The medical imaging probe attachment apparatus of claim 8, wherein the cannula handle assembly has a pair of longitudinally spaced leg members that are joined at respective ends by a central portion extending between the spaced leg members and each leg member has an end disposed at an outwardly spaced distance from the central portion, wherein one cannula clamp is disposed at an end of each leg portion member, and wherein when the cannula handle is received and retained by the cannula clamps, a hand space is configured to be provided between the cannula handle and the central portion.

10. The medical imaging probe attachment apparatus of claim 1, wherein the probe attachment has a probe clamp that is configured to removably attach the imaging probe to the probe holder assembly.

11. The medical imaging probe attachment apparatus of claim 1, wherein the probe attachment has one or more bosses that are arranged to be received by one or more corresponding boss receiving apertures on the imaging probe.

12. A medical imaging probe attachment apparatus, comprising:

a cannula handle assembly, the cannula handle assembly including a pair of spaced cannula clamps configured to receive and secure a cannula handle at spaced locations along the cannula handle for conjoined movement with the cannula handle assembly and with a cannula attached to the cannula handle extending in a cannula direction outwardly from the cannula handle assembly along a cannula axis, the cannula handle assembly further including a central portion extending between the spaced cannula clamps and defining a hand space between the central portion and the cannula handle when secured by the cannula clamps to permit a user to grasp the cannula handle for manipulation of the medical imaging probe attachment apparatus;

a rigid extension arm having opposite first and second ends and a length extending therebetween, the rigid extension arm attached at its first end to the cannula handle assembly for conjoined movement with the cannula handle assembly, the rigid extension arm extending outwardly from the cannula handle assembly in the cannula direction and at a spaced lateral distance from and parallel to the cannula axis;

wherein the second end of the rigid extension arm is fixed at the spaced lateral distance from the cannula axis;

wherein the rigid extension arm is adjustably connected at its first end to the cannula handle assembly to selectively adjust the length of the extension arm extending from the cannula handle assembly; and a probe holder assembly, the probe holder assembly attached to the second end of the rigid extension arm for conjoined movement with the cannula handle assembly, the probe holder assembly having a probe attachment that is configured to removably attach an imaging probe to the probe holder assembly with an imaging end of the imaging probe being located approximate to and facing in a direction toward a distal end of the cannula when the cannula is attached to the cannula handle assembly.

13. The medical imaging probe attachment apparatus of claim 12, wherein the probe holder assembly has an attachment fixture and a probe attachment subassembly, the attachment fixture being attached to the second end of the rigid extension arm for conjoined movement with the cannula handle assembly, the probe attachment subassembly being attached to the attachment fixture, and the probe attachment subassembly having the probe attachment; and wherein the probe attachment subassembly is slidingly connected to the attachment fixture to allow selective positioning of the probe attachment subassembly relative to the attachment fixture.

14. The medical imaging probe attachment apparatus of claim 13, wherein the probe attachment subassembly has a float member and a guide member, the float member has the probe attachment, the float member is operatively connected to the guide member such that the float member is capable of constrained up and down movement along a direction toward and away from the cannula axis; and wherein the float member is spring biased in a direction toward the cannula axis.

15. The medical imaging probe attachment apparatus of claim 12, wherein the pair of spaced cannula clamps each includes an aperture in which the cannula handle is removably receivable to attach the cannula handle to the cannula handle assembly for the conjoined movement with the cannula handle assembly.

16. The medical imaging probe attachment apparatus of claim 12, wherein the probe attachment has a probe clamp that is configured to removably attach the imaging probe to the probe holder assembly.

17. The medical imaging probe attachment apparatus of claim 12, wherein the probe attachment has one or more bosses that are arranged to be received by one or more corresponding boss receiving apertures on the imaging probe.

* * * * *